(12) United States Patent
Müller et al.

(10) Patent No.: US 8,785,659 B2
(45) Date of Patent: Jul. 22, 2014

(54) METHOD FOR THE PRODUCTION OF SULPHONYLPYRROLES AS HDAC INHIBITORS

(75) Inventors: Matthias Müller, Constance (DE); Bernd Müller, Constance (DE); Thomas Maier, Stockach (DE)

(73) Assignee: 4SC AG, Planegg-Martinsried (DE)

( * ) Notice: Subject to any disclaimer, the term of this patent is extended or adjusted under 35 U.S.C. 154(b) by 133 days.

(21) Appl. No.: 12/921,928

(22) PCT Filed: Mar. 11, 2009

(86) PCT No.: PCT/EP2009/052870
§ 371 (c)(1),
(2), (4) Date: Dec. 13, 2010

(87) PCT Pub. No.: WO2009/112529
PCT Pub. Date: Sep. 17, 2009

(65) Prior Publication Data
US 2011/0105568 A1      May 5, 2011

(30) Foreign Application Priority Data

Mar. 12, 2008   (EP) .................................... 08004567

(51) Int. Cl.
*C07D 207/48*      (2006.01)

(52) U.S. Cl.
CPC .................................... *C07D 207/48* (2013.01)
USPC ..................................................... 548/542

(58) Field of Classification Search
CPC .................................................... C07D 207/48
USPC ..................................................... 548/542
See application file for complete search history.

(56) References Cited

U.S. PATENT DOCUMENTS

| 5,534,654 A | 7/1996 | Ohtani et al. |
| 2008/0176848 A1 | 7/2008 | Maier et al. |

FOREIGN PATENT DOCUMENTS

| EP | 0570594 | | 11/1993 |
| WO | 9312075 | | 6/1993 |
| WO | WO 2005/087724 | * | 9/2005 |
| WO | WO 2006/097474 A1 | | 9/2006 |
| WO | WO 2007/039404 A1 | | 4/2007 |

OTHER PUBLICATIONS

March ("March's Advanced Organic Chemistry," 5th ed. (2001), chapter 10).*
Sittig ("Pharmaceutical Manufacturing Encyclopedia," 2nd ed. (1988), pp. 1124-1125).*
Porcheddu et al. ("Synthesis of oximes and hydroxamic acids," in The Chemistry of Hydroxylamines, Oximes, and Hydroxamic Acids, Eds. Rappoport and Liebman (2009), Ch. 6 provided).*
Watson et al. (Tetrahedron Lett., (2002) 43, p. 683-685).*
International Search Report of PCT/EP2009/052870 (May 18, 2009).
M. Ojika et al., "Structure and Synthesis of Reductiline, A Novel Metabolite From a Variant of Streptomyces Orientals," Tetrahedron Letters, vol. 23, No. 47 (1982) pp. 4977-4980.
Ando et al., Synthetic Communications: An International Journal for Rapid Communication of Synthetic Organic Chemistry—"A Facile Preparation of Aliphatic Hydroxamic Acid from N,N,O-Tris(Trimethylsilyl)Hydroxylanmine and Acid Chloride", Department of Chemistry, The University of Tsukuba, Niiharigun, Ibaraki, 305, Japan—Published online Feb. 6, 2007, Synthetic Communications, 13(12), 1053-1056 (1983).
Flemming, "Frontier Orbitals and Organic Chemical Reactions", Wiley, ISBN-10 0471018198)—Jan. 15, 1991.
Zhu et al., Synthetic Communications: An International Journal for Rapid Communications of Synthetic Organic Chemistry—"Reductions of Carboxylic Acids and Esters with NaBH4 in Diglyme at 162 C", University/Industry Chemical Research Center, Department of Chemistry, Mississippi State University, Mississippi State, Mississippi, Online Publication Date: Jan. 6, 2003, Synthetic Communications, vol. 33, No. 10, pp. 1733-1750 (2003).

(Continued)

*Primary Examiner* — Robert Havlin
(74) *Attorney, Agent, or Firm* — Millen, White, Zelano & Branigan, P.C.

(57) ABSTRACT

Process for the preparation of a compound of formula (I) wherein R1, R2, R3, R4, R5 and R6 have the meanings as defined in the specification, comprising the step of reacting an acrylic acid chloride compound of formula (II'): wherein R1, R2, R3, R4, R5 and R6 have the meanings as defined in the specification, with aqueous hydroxylamine and optionally converting the resulting compound into an acid addition salt thereof.

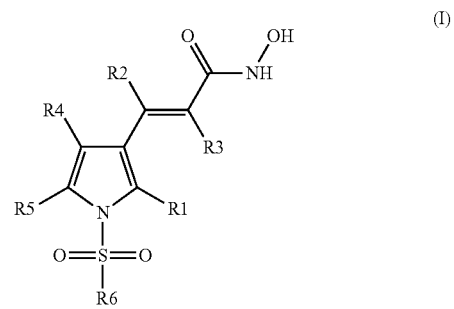

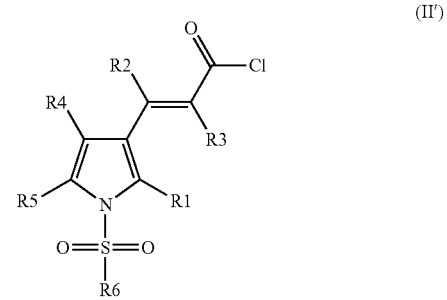

9 Claims, No Drawings

(56) References Cited

OTHER PUBLICATIONS

Hurd et al., "Rearrangement of Diphenyl-Para-Tolyl-Acethydroxamic Acid". Received Jul. 28, 1924—Published Jan. 8, 1925—Jones and Hurd, This Journal, 43, 2426 (1921)—vol. 47, pp. 174-178.

Partial Translation of Shin Jikkenkagakukouza, vol. 14, Synthesis and Reactions of Organic Compounds [II], Maruzen Co., Ltd., 1989, the 5th ed., pp. 1227-1228 (from line 5, p. 1227 to line 4, p. 1228).

* cited by examiner

METHOD FOR THE PRODUCTION OF SULPHONYLPYRROLES AS HDAC INHIBITORS

FIELD OF APPLICATION OF THE INVENTION

The invention relates to a novel production method of N-sulphonylpyrrole derivatives and salts thereof, which are used in the pharmaceutical industry for the production of pharmaceutical compositions.

TECHNICAL BACKGROUND

Transcriptional regulation in cells is a complex biological process. One basic principle is regulation by posttranslational modification of histone proteins, namely histone proteins H2A/B, H3 and H4 forming the octameric histone core complex. These complex N-terminal modifications at lysine residues by acetylation or methylation and at serine residues by phosphorylation constitute part of the so called "histone code" (Strahl & Ellis, Nature 403, 41-45, 2000). In a simple model, acetylation of positively charged lysine residues decreases affinity to negatively charged DNA, which now becomes accessible for the entry of transcription factors.

Histone acetylation and deacetylation is catalysed by histone acetyltransferases (HATs) and histone deacetylases (HDACs). HDACs are associated with transcriptional repressor complexes, switching chromatin to a transcriptionally inactive, silent structure (Marks et al. Nature Cancer Rev 1, 194-202, 2001). The opposite holds true for HATs which are associated with transcriptional activator complexes. Three different classes of HDACs have been described so far, namely class I (HDAC 1-3, 8) with Mr=42-55 kDa primarily located in the nucleus and sensitive towards inhibition by Trichostatin A (TSA), class II (HDAC 4-7, 9, 10) with Mr=120-130 kDa and TSA sensitivity and class III (Sir2 homologues) which are quite distinct by their NAD$^+$ dependency and TSA insensitivity.

Cancer chemotherapy was established based on the concept that cancer cells with uncontrolled proliferation and a high proportion of cells in mitosis are killed preferentially. Standard cancer chemotherapeutic drugs finally kill cancer cells upon induction of programmed cell death ("apoptosis") by targeting basic cellular processes and molecules, namely RNA/DNA (alkylating and carbamylating agents, platin analogs and topoisomerase inhibitors), metabolism (drugs of this class are named anti-metabolites) as well as the mitotic spindle apparatus (stabilizing and destabilizing tubulin inhibitors). Inhibitors of histone deacetylases (HDIs) constitute a new class of anti cancer drugs with differentiation and apoptosis inducing activity. By targeting histone deacetylases, HDIs effect histone (protein) acetylation and chromatin structure, inducing a complex transcriptional reprogramming, exemplified by reactivation of tumor suppressor genes and repression of oncogenes. Beside effecting acetylation of N-terminal lysine residues in core histone proteins, non-histone targets important for cancer cell biology like heat-shock-protein 90 (Hsp90) or the p53 tumor suppressor protein exist. The medical use of HDIs might not be restricted to cancer therapy, since efficacy in models for inflammatory diseases, rheumatoid arthritis and neurodegeneration was shown.

Benzoyl or acetyl substituted pyrrolyl propenamides are described in the public literature as HDAC-inhibitors, whereas the connectivity of the acyl-group is at position 2 or 3 of the pyrrole scaffold. (Mai et. al., Journal Med. Chem. 2004, Vol. 47, No. 5, 1098-1109; or Ragno et al., Journal Med. Chem. 2004, Vol. 47, No. 5, 1351-1359). Further pyrrolyl substituted hydroxamic acid derivatives are described in U.S. Pat. No. 4,960,787 as lipoxygenase inhibitors or in U.S. Pat. No. 6,432,999 as cyclooxygenase inhibitors or in EP570594 as inhibitors of cell growth.

Addressing the remaining need in the art for novel, well-tolerated and more efficacious inhibitors of HDACs, the international applications WO 2005/087724, WO 2007/039403 and WO 2007/039404 describe N-hydroxy-acrylamide derivatives of N-sulphonylpyrroles as HDAC inhibitors.

WO 2005/087724, WO 2007/039403 and WO 2007/039404 also disclose a process for the preparation of said N-hydroxy-acrylamide derivatives.

This preparation process comprises in the last step the synthesis of N-hydroxy-acrylamide derivatives starting from the corresponding acrylic acids. During said synthesis, the corresponding acrylic acid derivative is coupled with O-(tetrahydro-2H-pyran-2-yl)hydroxylamine by the reaction with an amide linking reagent (EDCxHCl and HOBtxH2O). After removal of the protecting group by stirring with an acid ion exchange resin, the respective N-hydroxy-acrylamide derivative is obtained:

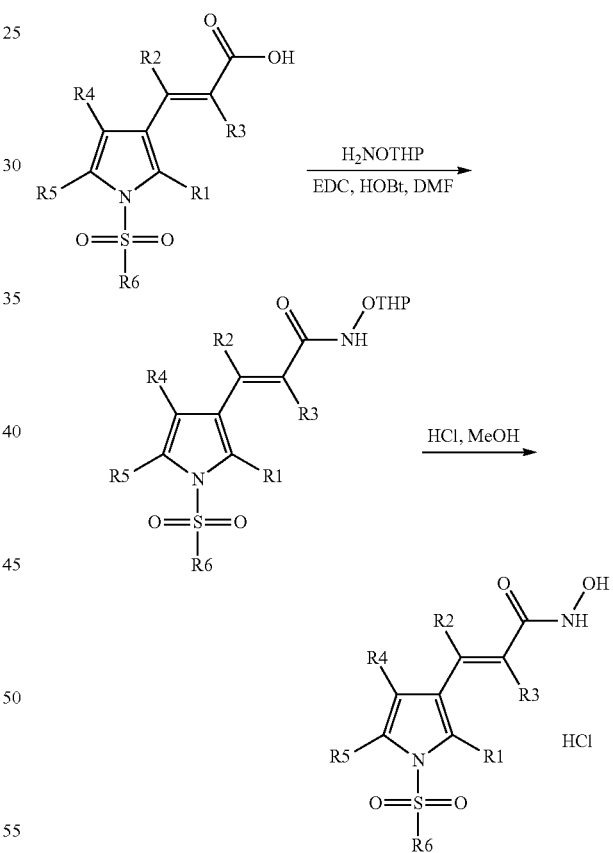

The use of O-(tetrahydro-2H-pyran-2-yl)hydroxylamine and EDCxHCl is, however, a disadvantage not only under cost aspects but also because these reagents are not available in large quantities. Furthermore, O-(tetrahydro-2H-pyran-2-yl)hydroxylamine is explosive and it is necessary to remove the byproducts an additional purification step, e.g. column chromatography.

An object of the invention therefore is to provide a commercially attractive, less expensive but at least equally effective process for preparing N-hydroxy-acrylamide derivatives of N-sulphonylpyrrole compounds, which derivatives have HDAC inhibitory activity, which allows obtaining the reaction product in fewer steps and with high yield and purity.

DESCRIPTION OF THE INVENTION

In accordance with a first aspect of the present invention a novel process for the preparation of N-hydroxy-acrylamide derivatives of N-sulphonylpyrrole compounds having HDAC inhibitory activity has now been developed, which is described in more detail below, comprising a step of transforming an acrylic acid chloride intermediate into the corresponding N-hydroxy acrylamide derivative. Surprisingly, this reaction can be conducted with aqueous hydroxylamine without the formation of acrylic acid by-products and leads to the formation of the free base of the corresponding N-hydroxy-acrylamide N-sulphonylpyrrole or its respective hydrochloride.

Said finding is especially surprising, as acid chlorides like the above intermediates are in general very susceptible towards hydrolysis upon contact with water. In this regard, the well-known textbook of Jerry March, Advanced Organic Chemistry [4$^{th}$ edition, 1992, p. 377] states the following: Acyl halides are so reactive that hydrolysis is easily carried out. In fact, most simple acyl halides must be stored under anhydrous conditions lest they react with water in the air. Consequently, water is usually a strong enough nucleophile for the reaction, though in difficult cases hydroxide ion may be required.

Even more surprisingly, the application of protected hydroxylamine as in the prior art process led to the formation of significant quantities of acrylic acid by-products.

Thus, the newly developed preparation process of N-hydroxy-acrylamide derivatives of N-sulphonylpyrrole compounds having HDAC inhibitory activity according to the present invention provides the advantages of being much more cost effective than the process known form the prior art and of enabling the direct formation of N-hydroxy-acrylamides without the necessity of the additional steps of deprotection and purification.

The present invention thus relates in a first general aspect to a novel process for the preparation of a compound of formula I, which is an N-hydroxy-acrylamide derivative of an N-sulphonylpyrrole compound and has HDAC inhibitory activity:

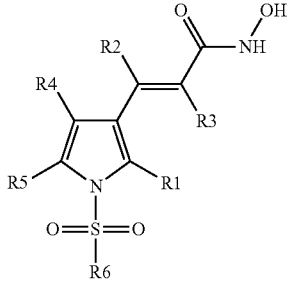

Formula I wherein
R1 is hydrogen, 1-4C-alkyl, halogen, or 1-4C-alkoxy,
R2 is hydrogen or 1-4C-alkyl,
R3 is hydrogen or 1-4C-alkyl,
R4 is hydrogen, 1-4C-alkyl, halogen, or 1-4C-alkoxy,
R5 is hydrogen, 1-4C-alkyl, halogen, or 1-4C-alkoxy,
R6 is -T1-Q1, wherein
T1 is a bond,
Q1 is Ar1, Aa1, Hh1, or Ah1, wherein
Ar1 is phenyl, or R61- and/or R62-substituted phenyl, wherein
R61 is 1-4C-alkyl, or -T2-N(R611)R612, wherein
either
T2 is a bond, and
R611 is 1-4C-alkyl, 1-4C-alkoxy-2-4C-alkyl, or phenyl-1-4C-alkyl,
R612 1-4C-alkyl, or 1-4C-alkoxy-2-4C-alkyl, or
R611 and R612 together and with inclusion of the nitrogen atom, to which they are bonded, form a heterocyclic ring Het1, wherein
Het1 is morpholino, thiomorpholino, S-oxo-thiomorpholino, S,S-dioxo-thiomorpholino, piperidino, or pyrrolidino,
or
T2 is 1-4C-alkylene, or 2-4C-alkylene interrupted by oxygen, and
R611 is 1-4C-alkyl, 1-4C-alkoxy-2-4C-alkyl, or phenyl-1-4C-alkyl,
R612 is 1-4C-alkyl, or 1-4C-alkoxy-2-4C-alkyl, or
R611 and R612 together and with inclusion of the nitrogen atom, to which they are bonded, form a heterocyclic ring Het1, wherein
Het1 is morpholino, thiomorpholino, S-oxo-thiomorpholino, S,S-dioxo-thiomorpholino, piperidino, pyrrolidino, imidazolo, pyrrolo or pyrazolo,
R62 is 1-4C-alkyl, 1-4C-alkoxy, halogen, cyano, 1-4C-alkoxy-1-4C-alkyl, 1-4C-alkylcarbonylamino, or 1-4C-alkylsulphonylamino,
Aa1 is a bisaryl radical made up of two aryl groups,
which are selected independently from a group consisting of phenyl and naphthyl, and
which are linked together via a single bond,
Hh1 is a bisheteroaryl radical made up of two heteroaryl groups,
which are selected independently from a group consisting of monocyclic 5- or 6-membered heteroaryl radicals comprising one or two heteroatoms, each of which is selected from the group consisting of nitrogen, oxygen and sulfur, and which are linked together via a single bond,
Ah1 is a heteroaryl-aryl radical or an aryl-heteroaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond,
wherein Aa1, Hh1 and Ah1 may be optionally substituted by R63 and/or R64, wherein
R63 is 1-4C-alkyl, phenyl-1-4C-alkyl, 1-4C-alkoxy, trifluoromethyl, cyano, halogen, completely or predominantly fluorine-substituted 1-4C-alkoxy, 1-4C-alkoxy-1-4C-alkyl, 1-4C-alkylsulphonylamino, tolylsulphonylamino, phenylsulphonylamino, 1-4C-alkylcarbonylamino, carbamoyl, mono- or di-1-4C-alkylaminocarbonyl, mono- or di-1-4C-alkylaminosulphonyl, or -T3-N(R631)R632, wherein
T3 is a bond, 1-4C-alkylene, or 2-4C-alkylene interrupted by oxygen, and
R631 is 1-4C-alkyl, 1-4C-alkoxy-2-4C-alkyl, or phenyl-1-4C-alkyl,
R632 1-4C-alkyl, or 1-4C-alkoxy-2-4C-alkyl, or
R631 and R632 together and with inclusion of the nitrogen atom, to which they are bonded, form a heterocyclic ring Het2, wherein Het2 is morpholine, thiomorpholino, S-oxo-thiomorpholino, S,S-dioxo-thiomorpholino, piperidino, pyrrolidino, imidazolo, pyrrolo or pyrazolo, and R64 is 1-4C-alkyl, 1-4C-alkoxy or halogen, comprising the step of reacting an acrylic acid chloride compound of formula II':

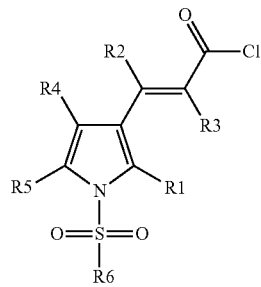

Formula II' wherein R1, R2, R3, R4, R5 and R6 have the meanings as defined above, with aqueous hydroxylamine and optionally converting the resulting compound into an acid addition salt thereof.

In a further aspect the present invention relates to a novel process for the preparation of a compound of formula I according to the first general aspect, further comprising the steps of i) providing a compound of formula II:

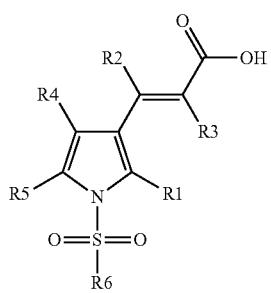

Formula II wherein R1, R2, R3, R4, R5 and R6 and have the meanings as defined above, and ii) transforming the compound of formula II into its acid chloride of formula II'.

In a third aspect the present invention relates to a process wherein the above step ii) is carried out with thionyl chloride or oxalyl chloride.

In a fourth aspect the present invention relates to a process wherein the above step i) is carried out by synthesizing the compound of formula II according to a process comprising the following steps:

lengthening the carbon chain of a compound of formula V:

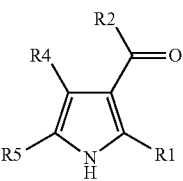

Formula V wherein R1, R2, R4 and R5 have the meanings as defined above, to obtain a compound of formula IV:

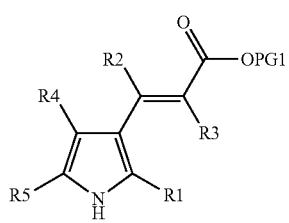

Formula IV wherein R1, R2, R3, R4 and R5 have the meanings as defined above and PG1 stands for a suitable temporary protective group for the carboxyl group, reacting the compound of formula IV with a compound of formula R6-SO$_2$— is X, wherein R6 is as defined above and X is a suitable leaving group, to give the corresponding compound of formula III:

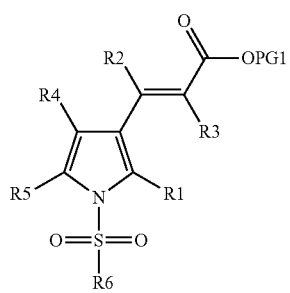

Formula III wherein R1, R2, R3, R4, R5 and R6 have the meanings as defined above and PG1 stands for a suitable temporary protective group for the carboxyl group, and removing the protective group PG1 to afford a compound of formula II.

In a fifth aspect the present invention relates to a process according to any of the preceding aspects, wherein the compound of formula I is obtained in the form of the free base.

In a sixth aspect the present invention relates to a process according to any of the aspects one to four, wherein the compound of formula I is directly obtained in the form of its hydrochloride salt by reaction of a compound of formula II' with aqueous hydroxylamine.

In a seventh aspect the present invention relates to a process according to any of the aspects one to four for the preparation of other salts of the compounds of formula I than the hydrochloride, comprising reacting the free base of a compound of formula I with a suitable acid or acid derivative to form the corresponding acid addition salt, or converting the acid addition salt of a compound of formula I into another acid addition salt.

In an eighth aspect the present invention relates to a process according to the seventh aspect, wherein the acid addition salt of the compounds of formula I other than the hydrochloride is the methanesulfonate.

In a ninth aspect the present invention relates to a process for preparing a pharmaceutical composition containing a compound of formula I or a pharmaceutically acceptable acid addition salt thereof, comprising synthesizing the compound of formula I or its acid addition salt according to any one of the preceding aspects and formulating the resulting compound with customary pharmaceutical excipients.

In a tenth aspect the present invention relates to a process according to the ninth aspect, wherein the pharmaceutical composition is for treating, preventing or ameliorating benign and/or malignant neoplasia, such as e.g. cancer, hyperproliferative diseases of benign or malignant behaviour and/or disorders responsive to induction of apoptosis.

Especially preferred is the preparation of the methanesulfonate salt of the compounds of formula I according to a process as described in any of the above aspects, in particular of
(E)-3-[1-(4-dimethylaminomethyl-benzenesulfonyl)-1H-pyrrol-3-yl]-N-hydroxy-acrylamide,
(E)-N-Hydroxy-3-[1-(5-pyridin-2-yl-thiophene-2-sulfonyl)-1H-pyrrol-3-yl]-acrylamide and
(E)-N-Hydroxy-3-{1-[4-(1-methyl-1H-pyrazol-4-yl)benzenesulfonyl]-1H-pyrrol-3-yl}-acrylamide.

Preferably, the chlorinating agent in a process according to the above aspects one to eight is utilized in a 2- to 3-fold molar excess related to the compound of formula II.

The temperature of the chlorinating reaction is preferably in the range between 40 and 60° C.

Even more preferably, aqueous hydroxylamine is utilized in a 10- to 30-fold molar excess related to the compound of formula II'.

The temperature of the amide forming step is in preferably in the range between 10 and 30° C., most preferably at room temperature.

In another preferred embodiment, the reaction mixture is stirred for 20-90 min after the completion of the addition of the compound of formula II' to the aqueous hydroxylamine containing solution.

In a most preferred embodiment of the invention, the methanesulfonate salt of any of the above listed three preferred compounds is prepared according to a process using the preferred reaction conditions as described in the preceding five paragraphs.

BEST MODE FOR CARRYING OUT THE INVENTION

The compounds of formula I can be prepared according to the following scheme by reacting the hydrochloride salt of the corresponding acrylic acid compounds of formula II with a chlorinating agent and adding the obtained acid chloride of formula II' to a solution of aqueous hydroxylamine and, preferably, THF:

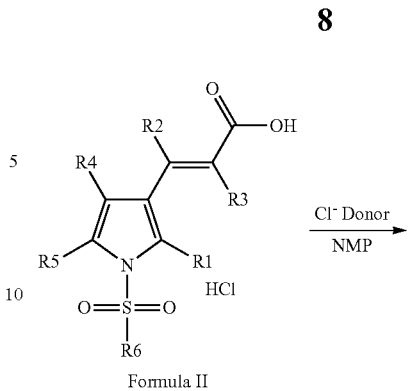

Thereby, the compounds of formula I precipitate either directly as free base or as hydrochloride salt, both of which can be easily isolated by filtration in high purity. If desired, the free base can be converted into its hydrochloride by reaction with hydrogen chloride. Similar procedures exist to prepare other acid addition salts and are well known to a skilled person.

Preferred examples of the chlorinating agent include, but are not limited to, $SOCl_2$ and $(COCl)_2$.

The compounds of formula II can be prepared according to the following reaction scheme:

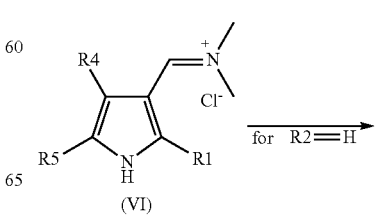

-continued

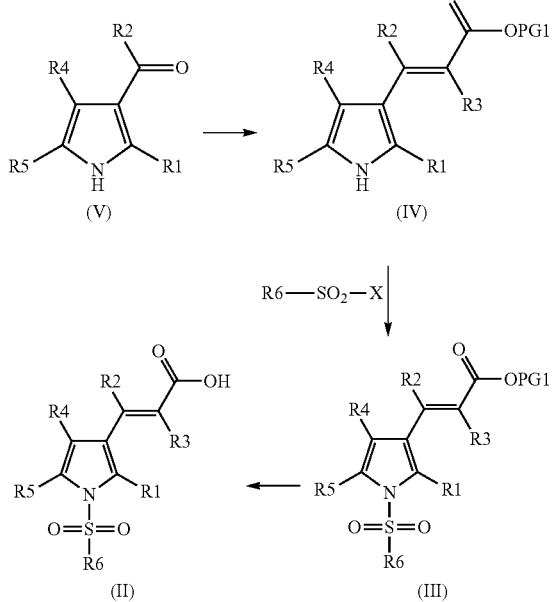

In the reaction scheme the carbon chain of a compound of formula V, wherein R1, R2, R4 and R5 have the meanings as defined above, is lengthened, for example, by a condensation reaction (with a malonic acid derivative) or by a Wittig or Julia reaction or, particularly in the case when R2 is hydrogen, by a Horner-Wadsworth-Emmons reaction (with a β-(alkoxy-carbonyl)-phosphonic acid dialkyl ester) to obtain a compound of formula IV, wherein R1, R2, R3, R4 and R5 have the meanings as defined above and PG1 stands for a suitable temporary protective group for the carboxyl group, for example tert-butyl or one of those art-known protective groups mentioned in "Protective Groups in Organic Synthesis" by T. Greene and P. Wuts (John Wiley & Sons, Inc. 1999, $3^{rd}$ Ed.) or in "Protecting Groups" (Thieme Foundations Organic Chemistry Series N Group" by P. Kocienski (Thieme Medical Publishers, 2000).

Compounds of formula V are known, or can be prepared according to art-known procedures, or can be obtained from compounds of formula VI, for the case that R2 is hydrogen.

Compounds of formula VI are known or are accessible in a known manner.

A compound of formula IV can be reacted with a compound of formula R6-$SO_2$—X, wherein R6 has the meanings as defined above and X is a suitable leaving group, such as e.g. chlorine, to give the corresponding compound of formula III, wherein R1, R2, R3, R4, R5, R6 and PG1 have the meanings as defined above.

Compounds of formula R6-$SO_2$—X are known or can be prepared in a known manner.

In the next reaction step, the protective group PG1 of a compound of formula III can be removed according to an art-known manner to yield a compound of formula II.

A compound of formula II' can be obtained by reacting a compound of formula II with thionyl chloride or oxalyl chloride. The reaction can optionally be carried out as an in-situ process without isolating the compound of formula II'. That is, the compound of formula II' can without isolation be reacted with aqueous hydroxylamine to form a compound of formula I.

The present invention is meant to include both variants, i.e. the in-situ formation of a compound of formula I from a compound of formula II by way of reacting the non-isolated intermediate of formula II' with aqueous hydroxylamine and the reaction of the isolated intermediate of formula II' with aqueous hydroxylamine to form a compound of formula I. The in-situ process is preferred.

Optionally, the free base form of a compound of formula I can be converted into one of its acid addition salts. Furthermore, the hydrochloride of a compound of formula I or any other acid addition salt thereof can be converted into its free base form.

Salts can be obtained by dissolving the free base form of the compounds of formula I in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low molecular weight aliphatic alcohol such as ethanol or isopropanol) which contains the desired acid or base, or to which the desired acid or base is then added. The salts can then be obtained by filtering, reprecipitating, precipitating with a nonsolvent for the addition salt (e.g. isopropanol, acetone or acetonitrile) or by evaporating the solvent.

The free base form of the compounds of formula I can be obtained from its hydrochloride salt by alkalization and can then be further converted into other salts as described above.

In this way, pharmacologically acceptable salts can be obtained.

The following examples serve to illustrate the invention further without restricting it.

EXAMPLES (E)-3-[1-(4-dimethylaminomethyl-benzenesulfonyl)-1H-pyrrol-3-yl]-N-hydroxy-acrylamide hydrochloride

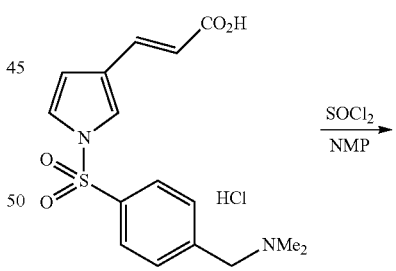

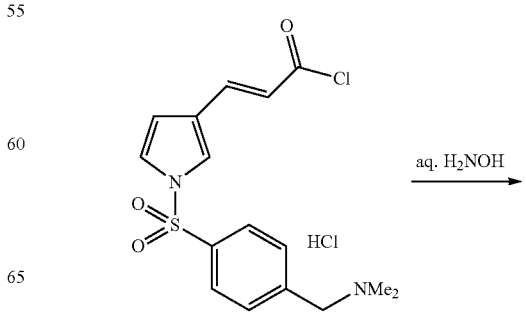

11
-continued

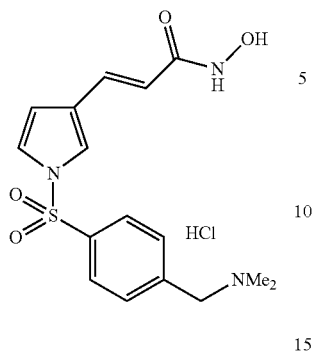

A reaction vessel was charged with (E)-3-[1-(4-dimethylaminomethyl-benzenesulfonyl)-1H-pyrrol-3-yl]-acrylic acid hydrochloride (20.0 kg, 53.92 mol), hyflow (10.0 kg) and 1-methyl-2-pyrrolidone (130.0 L). The suspension was heated to 60-68° C., stirred for 15-45 min and filtered. The filter cake was washed with 1-methyl-2-pyrrolidone (10.0 L) and the filtrate was transferred into a reaction vessel. The solution was heated to 40-50° C. and thionyl chloride (19.0 kg, 159.94 mol) was added over a period of 1-1.5 h. After stirring for 20-45 min, the acid chloride solution was cooled to 18-28° C.

A second reaction vessel was charged with aqueous hydroxylamine (50%, 42.8 kg, 647 mol) and THF (40.0 L). The above prepared solution of (E)-3-[1-(4-dimethylaminomethyl-benzenesulfonyl)-1H-pyrrol-3-yl]-acryloyl chloride hydrochloride was added at 18-30° C. over a period of 2-4 h. After stirring for 20-40 min, acetone (47.6 L, 647 mmol) was added at 17-25° C. within 45-90 min. The reaction mixture was stirred for 30 min and acetonitrile (570.0 L) was added over a period of 1-2 h. The suspension was stirred at 17-25° C. for at least 4 h, cooled to 5-13° C. and stirred for 1-2 h. The solid was centrifuged and was used without further drying in the subsequent free basing step.

(E)-N-Hydroxy-3-[1-(5-pyridin-2-yl-thiophene-2-sulfonyl)-1H-pyrrol-3-yl]-acrylamide

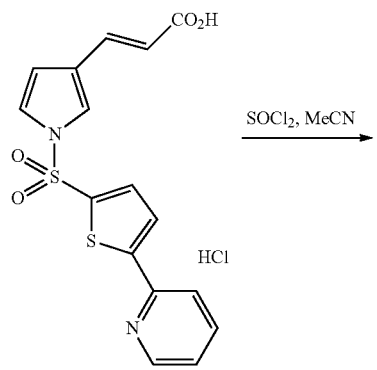

12
-continued

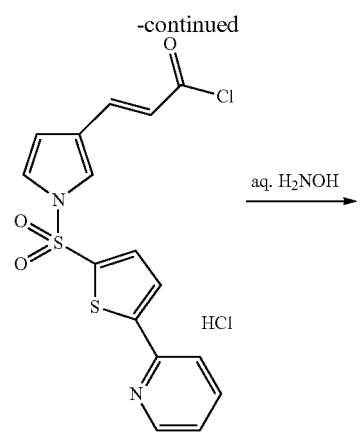

(E)-3-[1-(5-Pyridin-2-yl-thiophene-2-sulfonyl)-1H-pyrrol-3-yl]-acrylic acid hydrochloride (30.0 g, 75.6 mmol) was suspended in acetonitrile (540 mL) and thionyl chloride (12.1 mL, 166.3 mmol) was added over a period of 10 min. The suspension was heated to 60° C. and stirred for 2 h.

The above prepared solution of (E)-3-[1-(5-Pyridin-2-yl-thiophene-2-sulfonyl)-1H-pyrrol-3-yl]-acryloyl chloride hydrochloride was added to an aqueous hydroxylamine solution (50%, 150 g, 2.27 mop at 20-25° C. over a period of 45 min. After stirring for 65 min, water (300 mL) was added and cooled to 0° C. The suspension was filtered and the filter cake was washed with water (150 mL). The title compound was obtained as beige solid (17.3 g).

(E)-N-Hydroxy-3-{1-[4-(1-methyl-1H-pyrazol-4-yl)-benzenesulfonyl]-1H-pyrrol-3-yl}-acrylamide

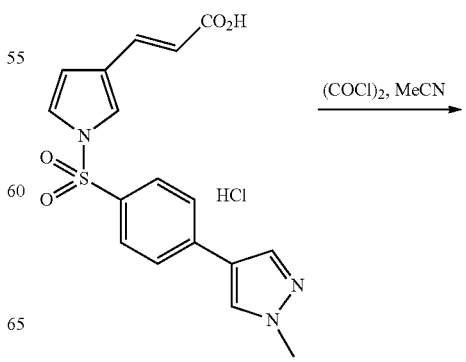

-continued

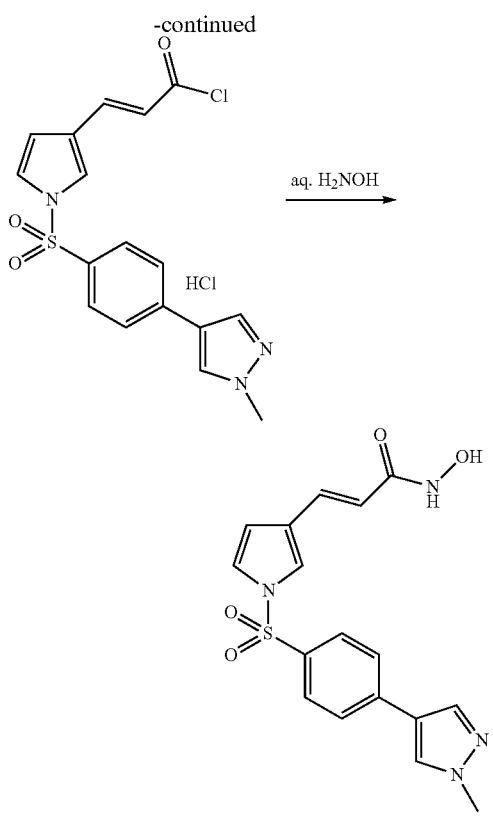

(E)-3-{1-[4-(1-Methyl-1H-pyrazol-4-yl)-benzenesulfonyl]-1H-pyrrol-3-yl}-acrylic acid hydrochloride (70.0 g, 177.7 mmol) was suspended in acetonitrile (525 mL) and oxalyl chloride (31.5 mL, 355.4 mmol) was added within 5 min. The suspension was heated to 55° C. and stirred for 1 h.

The above prepared solution of (E)-3-{1-[4-(1-Methyl-1H-pyrazol-4-yl)-benzenesulfonyl]-1H-pyrrol-3-yl}-acryloyl chloride hydrochloride was added to an aqueous hydroxylamine solution (50%, 105 mL, 1.78 mol) at 10-20° C. over a period of 20 min. After stirring for 90 min, the suspension was filtered and dried. The crude product (48.4 g) was suspended in a mixture of isopropanol (480 mL) and water (480 mL) and stirred at reflux for 1 h. After cooling to room temperature, the suspension was filtered and dried. The title compound was obtained as beige solid (28.1 g).

Commercial Utility

The compounds as prepared according to this invention have valuable pharmacological properties by inhibiting histone deacetylase activity and function. They cause hyperacetylation of certain substrate proteins and as functional consequence for example the induction or repression of gene expression, induction of protein degration, cell cycle arrest, induction of differentiation and/or induction of apoptosis.

The term "induction of apoptosis" and analogous terms are used to identify a compound which executes programmed cell death in cells contacted with that compound. Apoptosis is defined by complex biochemical events within the contacted cell, such as the activation of cystein specific proteinases ("caspases") and the fragmentation of chromatin. Induction of apoptosis in cells contacted with the compound might not necessarily be coupled with inhibition of cell proliferation or cell differentiation. Preferably, the inhibition of proliferation, induction of differentiation and/or induction of apoptosis is specific to cells with aberrant cell growth.

"Induction of differentiation" is defined as a process of cellular reprogramming leading to a reversible or irreversible cell cycle arrest in G0 and re-expression of a subset of genes typical for a certain specialized normal cell type or tissue (e.g. re-expression of milk fat proteins and fat in mammary carcinoma cells).

The invention further relates to a process for preparing a pharmaceutical composition for inhibiting, treating, ameliorating or preventing cellular neoplasia. A "neoplasia" is defined by cells displaying aberrant cell proliferation and/or survival and/or a block in differentiation. The term neoplasia includes "benign neoplasia" which is described by hyperproliferation of cells, incapable of forming an aggressive, metastasizing tumor in vivo, and, in contrast, "malignant neoplasia" which is described by cells with multiple cellular and biochemical abnormalities, capable of forming a systemic disease, for example forming tumor metastasis in distant organs.

The pharmaceutical compositions prepared according to the present invention are preferably used for the treatment of malignant neoplasia, also described as cancer, characterized by tumor cells finally metastasizing into distinct organs or tissues. Examples of malignant neoplasia treated with the N-sulphonylpyrrole derivatives of the present invention include solid and hematological tumors. Solid tumors are exemplified by tumors of the breast, bladder, bone, brain, central and peripheral nervus system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasia include inherited cancers exemplified by Retinoblastoma and Wilms tumor. In addition, malignant neoplasia include primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies.

The invention further provides a method for preparing pharmaceutical compositions for treating a mammal, in particular a human, bearing a disease different to cellular neoplasia, sensitive to histone deacetylase inhibitor therapy. These non malignant diseases include (i) arthropathies and osteopathological conditions or diseases such as rheumatoid arthritis, osteoarthrtis, gout, polyarthritis, and psoriatic arthritis, (ii) autoimmune diseases like systemic lupus erythematosus and transplant rejection, (iii) hyperproliferative diseases such as smooth muscle cell proliferation including vascular proliferative disorders, atherosclerosis and restenosis, (iv) acute and chronic inflammatory conditions or diseases and dermal conditions such as ulcerative colitis, Crohn's disease, allergic rhinitis, allergic dermatitis, cystic fibrosis, chronic obstructive bronchitis and asthma, (v) endometriosis, uterine fibroids, endometrial hyperplasia and benign prostate hyperplasia, (vi) cardiac dysfunction, (vii) inhibiting immunosuppressive conditions like HIV infections,
(viii) neuropathological disorders like Parkinson's disease, Alzheimer disease or polyglutamine related disorders, and
(ix) pathological conditions amenable to treatment by potentiating of endogenous gene expression as well as enhancing transgene expression in gene therapy.

The process of the present invention provides compounds in purified or substantially pure form, such as e.g. greater than about 50%, more preferably about 60%, more preferably about 70%, more preferably about 80%, more preferably about 90%, more preferably about 95%, more preferably about 97%, more preferably about 99% wt purity as determined by art-known methods.

The pharmaceutical compositions prepared according to the present invention are in solid or liquid form, particularly solid oral dosage forms, such as tablets and capsules, as well as suppositories and other pharmaceutical dosage forms. They comprise one or more of the compounds of formula I and a pharmaceutically acceptable excipient. Optionally, a further active ingredient, particularly, a further anti-cancer drug, can be present.

The pharmaceutical compositions prepared according to this invention can have histone deacetylases inhibitory activity, apoptosis inducing activity, anti-proliferative effects and/or cell-differentiation inducing activity.

Pharmaceutical compositions containing a compound of formula I prepared according to this invention are formulated by processes which are known per se and familiar to the person skilled in the art. As pharmaceutical compositions, the compounds of formula I (=active compounds) are employed in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with excipients (i.e. auxiliaries, vehicles, diluents, carriers or adjuvants) which are suitable for the desired pharmaceutical formulations, preparations or compositions on account of his/her expert knowledge. In addition to solvents, gel formers, ointment bases other excipients, for example antioxidants, dispersants, emulsifiers, preservatives, solubilizers, colorants, complexing agents or permeation promoters, can be used.

The person skilled in the art is aware on the base of his/her expert knowledge of the kind, total daily dosage(s) and administration form(s) of the compound of formula I and any additional therapeutic agent(s) coadministered. Said total daily dosage(s) can vary within a wide range.

As for suitable combinations for co-administration, dosage regimens, medicaments, kits-of-parts, commercial packages, methods of treatment etc. of compounds according to formula I, reference is made to WO 2007/039404, the disclosure of which is hereby incorporated in its entirety, particularly to pages 88-96.

The administration of the compounds prepared according to this invention, the combinations and pharmaceutical compositions prepared according to the invention may be performed in any of the generally accepted modes of administration available in the art. Illustrative examples of suitable modes of administration include intravenous, oral, nasal, parenteral, topical, transdermal and rectal delivery. Oral and intravenous delivery is preferred. For further detail, reference is made to WO 2007/039404, particularly to page 87, penultimate paragraph.

The invention claimed is:
1. A process for preparing a compound of formula I:

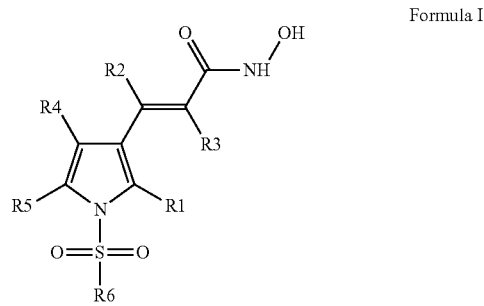

Formula I wherein
R1 is hydrogen,
R2 is hydrogen,
R3 is hydrogen,
R4 is hydrogen,
R5 is hydrogen,
R6 is -T1-Q1,
T1 is a bond,
Q1 is Ar1, Aa1, Hh1, or Ah1,
Ar1 is phenyl, or R61- and/or R62-substituted phenyl,
R61 is 1-4C-alkyl, or -T2-N(R611)R612,
either
T2 is a bond, and
R611 is 1-4C-alkyl, 1-4C-alkoxy-2-4C-alkyl, or phenyl-1-4C-alkyl,
R612 1-4C-alkyl, or 1-4C-alkoxy-2-4C-alkyl, or
R611 and R612 together and with inclusion of the nitrogen atom, to which they are bonded, form a heterocyclic ring Het1,
Het1 is morpholino, thiomorpholino, S-oxo-thiomorpholino, S,S-dioxo-thiomorpholino, piperidino, or pyrrolidino,
or
T2 is 1-4C-alkylene, or 2-4C-alkylene interrupted by oxygen, and
R611 is 1-4C-alkyl, 1-4C-alkoxy-2-4C-alkyl, or phenyl-1-4C-alkyl,
R612 is 1-4C-alkyl, or 1-4C-alkoxy-2-4C-alkyl, or
R611 and R612 together and with inclusion of the nitrogen atom, to which they are bonded, form a heterocyclic ring Het1,
Het1 is morpholino, thiomorpholino, S-oxo-thiomorpholino, S,S-dioxo-thiomorpholino, piperidino, pyrrolidino, imidazole, pyrrolo or pyrazolo, R62 is 1-4C-alkyl, 1-4C-alkoxy, halogen, cyano, 1-4C-alkoxy-1-4C-alkyl, 1-4C-alkylcarbonylamino, or 1-4C-alkylsulphonylamino, Aa1 is a bisaryl radical made up of two aryl groups, which are independently selected from the group consisting of phenyl and naphthyl, and which are linked together via a single bond, Hh1 is a bisheteroaryl radical made up of two heteroaryl groups, which are independently selected from the group consisting of monocyclic 5- or 6-membered heteroaryl radicals comprising one or two heteroatoms, each of which is selected from the group consisting of nitrogen, oxygen and sulfur, and which are linked together via a single bond, Ah1 is a heteroaryl-aryl radical or an aryl-heteroaryl radical made up of a heteroaryl group selected from the group consisting of monocyclic 5- or 6-membered heteroaryl radicals comprising one or two heteroatoms, each of which is selected from the group consisting of nitrogen, oxygen and sulfur, and an aryl group selected from the group consisting of phenyl and naphthyl, wherein said heteroaryl and aryl groups are linked together via a single bond, wherein Aa1, Hh1 and Ah1 may be optionally substituted by R63 and/or R64, R63 is 1-4C-alkyl, phenyl-1-4C-alkyl, 1-4C-alkoxy, trifluoromethyl, cyano, halogen, completely or predominantly fluorine-substituted 1-4C-alkoxy, 1-4C-alkoxy-1-4C-alkyl, 1-4C-alkylsulphonylamino, tolylsulphonylamino, phenylsulphonylamino, 1-4C-alkylcarbonylamino, carbamoyl, mono- or di-1-4C-alkylaminocarbonyl, mono- or di-1-4C-alkylaminosulphonyl, or -T3-N(R631)R632, T3 is a bond, 1-4C-alkylene, or 2-4C-alkylene interrupted by oxygen, R631 is 1-4C-alkyl, 1-4C-alkoxy-2-4C-alkyl, or phenyl-1-4C-alkyl, R632 1-4C-alkyl, or 1-4C-alkoxy-2-4C-alkyl, or R631 and R632 together and with inclusion of the nitrogen atom, to which they are bonded, form a heterocyclic ring Het2, Het2 is morpholino, thiomorpholino, S-oxo-thiomorpholino, S,S-dioxo-thiomorpholino, piperidino, pyrrolidino, imidazole, pyrrolo or pyrazolo, and R64 is 1-4C-alkyl, 1-4C-alkoxy or halogen, comprising reacting an acrylic acid chloride compound of formula II':

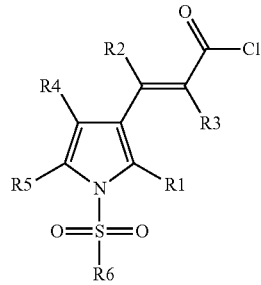

Formula II' wherein R1, R2, R3, R4, R5 and R6 have the meanings as defined for the compound of formula I,
with aqueous hydroxylamine, and
optionally converting the resulting compound into an acid addition salt thereof.

2. A process according to claim 1, further comprising
i) providing a compound of formula II:

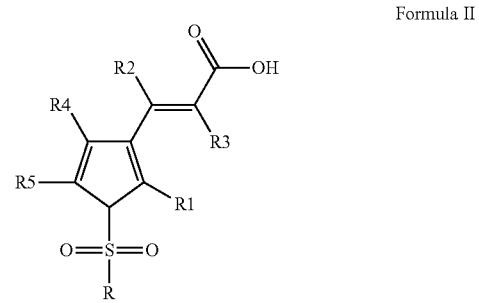

Formula II wherein R1, R2, R3, R4, R5 and R6 and have the meanings as defined for the compound of formula I,
and
ii) converting the compound of formula II into its acid chloride of formula II'.

3. A process according to claim 2, wherein ii) is carried out with thionyl chloride or oxalyl chloride.

4. A process according to claim 2, wherein i) is carried out by synthesizing the compound of formula II by converting a compound of formula V:

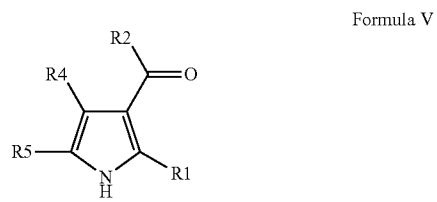

Formula V wherein R1, R2, R4 and R5 have the meanings as defined for the compound of formula II, to a compound of formula IV:

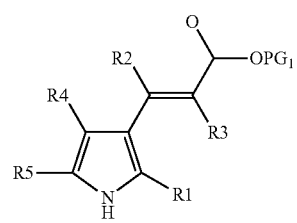

Formula IV wherein R1, R2, R3, R4 and R5 have the meanings as defined for the compound of formula II and PG1 stands for a temporary protective group for the carboxyl group,
and
reacting the compound of formula IV with a compound of formula R6-SO$_2$—X, wherein R6 is as defined for the compound of formula II and X is a leaving group, to give a compound of formula III:

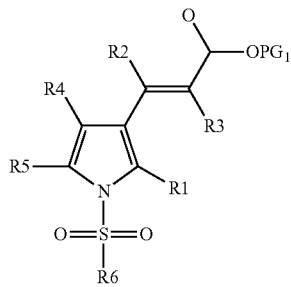

Formula III wherein R1, R2, R3, R4 and R6 have the meanings as defined for the compound of formula II and PG1 stands for a temporary protective group for the carboxyl group, and removing the protective group PG1 to obtain a compound of formula II.

5. A process according to claim 1 wherein the compound of formula I is obtained in the form of the free base.

6. A process according to claim 1 wherein the compound of formula I is directly obtained in the form of its hydrochloride salt by reaction of a compound of formula II' with aqueous hydroxylamine.

7. A process according to claim 1 for the preparation of a salt of a compound of formula I other than the hydrochloride, comprising reacting the free base of a compound of formula I with an acid or acid derivative to form the corresponding acid addition salt, or converting the acid addition salt of a compound of formula I into another acid addition salt.

8. A process according to claim 7, wherein the acid addition salt of the compounds of formula I other than the hydrochloride is the methanesulfonate.

9. A process for preparing a pharmaceutical composition containing a compound of formula I or a pharmaceutically acceptable acid addition salt thereof, comprising synthesizing the compound of formula I or its acid addition salt according to claim 1 and formulating the resulting compound with a pharmaceutically acceptable excipient.

* * * * *